United States Patent
Akmenkalns

(10) Patent No.: US 11,147,761 B2
(45) Date of Patent: Oct. 19, 2021

(54) TOPICAL SUPPLEMENT COMPOSITION AND METHOD OF USE

(71) Applicant: Nicole Akmenkalns, Youngsville, LA (US)

(72) Inventor: Nicole Akmenkalns, Youngsville, LA (US)

( * ) Notice: Subject to any disclaimer, the term of this patent is extended or adjusted under 35 U.S.C. 154(b) by 166 days.

(21) Appl. No.: 16/678,614

(22) Filed: Nov. 8, 2019

(65) Prior Publication Data

US 2020/0069573 A1    Mar. 5, 2020

Related U.S. Application Data

(63) Continuation of application No. 16/229,761, filed on Dec. 21, 2018, now abandoned.

(60) Provisional application No. 62/616,627, filed on Jan. 12, 2018.

(51) Int. Cl.

| | |
|---|---|
| *A61K 9/00* | (2006.01) |
| *A61K 8/67* | (2006.01) |
| *A61K 8/27* | (2006.01) |
| *A61K 8/19* | (2006.01) |
| *A61K 8/92* | (2006.01) |
| *A61K 8/44* | (2006.01) |
| *A61K 36/87* | (2006.01) |
| *A61K 31/4415* | (2006.01) |
| *A61K 47/20* | (2006.01) |
| *A61K 36/889* | (2006.01) |
| *A61K 33/26* | (2006.01) |
| *A61K 31/07* | (2006.01) |
| *A61K 36/73* | (2006.01) |
| *A61K 31/714* | (2006.01) |
| *A61K 47/10* | (2017.01) |
| *A61K 47/26* | (2006.01) |
| *A61K 33/06* | (2006.01) |
| *A61K 33/34* | (2006.01) |
| *A61K 31/122* | (2006.01) |
| *A61K 31/355* | (2006.01) |
| *A61K 47/44* | (2017.01) |
| *A61K 33/30* | (2006.01) |
| *A61K 31/375* | (2006.01) |
| *A61K 31/51* | (2006.01) |
| *A61K 33/20* | (2006.01) |
| *A61K 33/04* | (2006.01) |
| *A61K 31/525* | (2006.01) |
| *A61K 31/593* | (2006.01) |
| *A61K 33/18* | (2006.01) |
| *A61P 3/02* | (2006.01) |

(52) U.S. Cl.
CPC ............ *A61K 9/0014* (2013.01); *A61K 31/07* (2013.01); *A61K 31/122* (2013.01); *A61K 31/355* (2013.01); *A61K 31/375* (2013.01); *A61K 31/4415* (2013.01); *A61K 31/51* (2013.01); *A61K 31/525* (2013.01); *A61K 31/593* (2013.01); *A61K 31/714* (2013.01); *A61K 33/04* (2013.01); *A61K 33/06* (2013.01); *A61K 33/18* (2013.01); *A61K 33/20* (2013.01); *A61K 33/26* (2013.01); *A61K 33/30* (2013.01); *A61K 33/34* (2013.01); *A61K 36/73* (2013.01); *A61K 36/87* (2013.01); *A61K 36/889* (2013.01); *A61K 47/10* (2013.01); *A61K 47/20* (2013.01); *A61K 47/26* (2013.01); *A61K 47/44* (2013.01); *A61P 3/02* (2018.01)

(58) Field of Classification Search
None
See application file for complete search history.

(56) References Cited

U.S. PATENT DOCUMENTS

| | | | | | |
|---|---|---|---|---|---|
| 4,743,442 | A | * | 5/1988 | Raaf ........................ | A61K 8/44 424/47 |
| 4,966,169 | A | * | 10/1990 | Waddell ................. | A24B 15/30 131/31 |
| 5,084,482 | A | * | 1/1992 | Hirsch ................. | A61K 31/195 424/641 |
| 5,308,621 | A | | 5/1994 | Taylor et al. | |
| 5,639,797 | A | * | 6/1997 | Kropke .................... | A61K 8/06 424/78.03 |
| 6,074,652 | A | * | 6/2000 | Ishiwatari ................ | A61Q 1/10 424/401 |
| 6,077,828 | A | * | 6/2000 | Abbruzzese .......... | A23L 33/175 514/5.5 |
| 6,495,177 | B1 | * | 12/2002 | deVries ................... | A23L 33/15 424/439 |

(Continued)

FOREIGN PATENT DOCUMENTS

| | | | | |
|---|---|---|---|---|
| BE | 1005939 A6 | * | 3/1994 | ........... A61K 8/4953 |
| WO | WO-8402845 A1 | * | 8/1984 | ........... A61K 36/886 |

OTHER PUBLICATIONS

Burke, K. E. "Photodamage of the skin: protection and reversal with topical antioxidants." Journal of Cosmetic Dermatology 3.3 (2004): 149-155. (Year: 2004).*
Delalle-Lozica, Nevia. "Local therapy as basic anti-aging prevention." Acta Clinica Croatica 49.4 (2010): 529-536. (Year: 2010).*
Author Affiliations & NotesRosalind C. VoOphthalmology, Loma Linda University Medical Center, Loma Linda, CaliforniaJohn C. AffeldtOphthalmology, Loma Linda University Medical Center, Loma Linda, CaliforniaOcular Surface Center, Doheny Eye Institute, Los Angeles, CaliforniaFootnotesCommercial Relationships Rosalind C. Vo, None; John C. Affeldt, NoneMarch 2012Transdermal Vitamin A: a novel treatment for xerophthalmia?https://iovs.arvojournals.org/article.aspx?articleid=2353086.

(Continued)

*Primary Examiner* — Bethany P Barham
*Assistant Examiner* — Peter Anthopolos
(74) *Attorney, Agent, or Firm* — Boudwin Intellectual Property; Daniel Boudwin

(57) ABSTRACT

A topical supplement composition. The topical supplement composition includes one or more vitamins, minerals, or other nutrients, in combination with one or more suitable transdermal carriers. The topical supplement composition delivers vitamins, minerals or other nutrients via transdermal application from an individual's skin to the individual's bloodstream.

18 Claims, No Drawings

(56) References Cited

U.S. PATENT DOCUMENTS

| | | | | |
|---|---|---|---|---|
| 6,509,326 | B1* | 1/2003 | Andon | A23L 2/39 514/167 |
| 6,521,247 | B1* | 2/2003 | deVries | A23L 33/15 424/439 |
| 6,558,710 | B1* | 5/2003 | Godfrey | A61P 17/00 424/642 |
| 6,821,780 | B2* | 11/2004 | Thorel | A61K 8/19 435/325 |
| 7,025,955 | B2* | 4/2006 | Siddiqui | A61K 8/9789 424/70.1 |
| 7,060,306 | B2* | 6/2006 | Springstead | A61K 36/15 424/725 |
| 7,820,148 | B2* | 10/2010 | Thorel | A61K 8/44 424/70.1 |
| 8,491,940 | B2* | 7/2013 | Remington | A61K 36/889 424/725 |
| 8,552,063 | B2* | 10/2013 | Spencer | A61P 43/00 514/560 |
| 8,980,344 | B2* | 3/2015 | Gross | A61K 8/4953 424/777 |
| 8,992,953 | B2* | 3/2015 | Clavel | A61K 8/922 424/401 |
| 9,144,534 | B2* | 9/2015 | Pratt | A45D 7/04 |
| 9,326,932 | B2* | 5/2016 | Lewis, II | A61K 8/678 |
| 9,439,841 | B2* | 9/2016 | Wegner | A61K 8/345 |
| 9,468,596 | B2* | 10/2016 | Eizen | A61Q 19/007 |
| 9,474,709 | B2* | 10/2016 | Sams | A61K 8/67 |
| 9,839,604 | B1* | 12/2017 | Tabibian | A61K 31/52 |
| 10,493,018 | B1* | 12/2019 | Lincoln | A61Q 19/00 |
| 2002/0018788 | A1* | 2/2002 | Jutila | A61Q 9/04 424/400 |
| 2002/0022040 | A1 | 2/2002 | Robinson et al. | |
| 2002/0034484 | A1* | 3/2002 | Lacharriere | A61P 17/14 424/70.1 |
| 2003/0147825 | A1 | 8/2003 | Chiarelli et al. | |
| 2004/0043043 | A1 | 3/2004 | Schlyter et al. | |
| 2004/0171578 | A1* | 9/2004 | Klingelholler | A61P 17/04 514/52 |
| 2004/0258722 | A1* | 12/2004 | Kropke | A61Q 17/04 424/401 |
| 2005/0048139 | A1* | 3/2005 | Modak | A61K 8/27 424/725 |
| 2006/0263399 | A1* | 11/2006 | Yasuno | A61K 8/676 424/401 |
| 2008/0069779 | A1 | 3/2008 | Tamarkin et al. | |
| 2008/0253973 | A1 | 10/2008 | Tamarkin et al. | |
| 2009/0117061 | A1* | 5/2009 | Gross | A61K 8/31 424/59 |
| 2011/0008308 | A1* | 1/2011 | Taylor | A61Q 19/00 424/94.1 |
| 2014/0072671 | A1* | 3/2014 | Auerbach | A23L 33/15 426/72 |
| 2016/0128924 | A1* | 5/2016 | Lee | A61K 8/678 424/777 |
| 2016/0199292 | A1* | 7/2016 | Farnum | A61Q 19/007 424/55 |
| 2016/0287658 | A1* | 10/2016 | Son | A61K 9/4858 |
| 2017/0281527 | A1* | 10/2017 | Ronen | A61K 8/19 |
| 2018/0110721 | A1* | 4/2018 | Bell | A61K 8/9789 |
| 2019/0008755 | A1* | 1/2019 | Torok | A61K 8/97 |
| 2019/0060212 | A1* | 2/2019 | Aleksandrovich | A61K 8/44 |

OTHER PUBLICATIONS

Nesvadbova, Martina, et al. "Povidone iodine skin absorption: an ex-vivo study." Toxicology Letters 235.3 (2015): 155-160.

A. E. Schaefer H. L. Sassaman A. Slocum R. D. GreeneJun. 1, 1956Absorption of Topically Applied Vitamins: Two Figureshttps://academic.oup.com/jn/artide-abstract/59/2/171/4776301?redirectedFrom=PDF.

Alexander J. Michels, Ph.D. Linus Pauling Institute Oregon State UniversityFeb. 2012Vitamin E and Skin Healthhttps://lpi.oregonstate.edu/mic/health-disease/skin-health/vitamin-E#authors-reviewers.

Author Information: Department of Dermatology, STD and Leprosy, Government Medical College and Associated SMHS Hospital, Srinagar, Jammu and Kashmir, IndiaAddress for correspondence: Dr. Mohammad Abid Keen, Iqbal Abad, KP Road, Anantnag—192 101, Jammu and Kashmir, India. E-mail: moc.liamg@13dibaneek2016 Jul-Aug;Vitamin E in derrnatologyhttps://www.ncbi.nim.nih.gov/pmc/articles/PMC4976416/.

Author Information: Department of Pharmaceutical Sciences, Albany College of Pharmacy and Health Sciences, 106 New Scotland Avenue, Albany, New York 12208 USAFlorin Marcel Musteata, Phone: +1-(518)694-7883, Email: ude.shpca@ataetsum.lecram. corresponding authorCorresponding author.Published online Jan. 22, 2015.Investigating Transdermal Delivery of Vitamin D3https://www.ncbi.nlm.nih.gov/pmc/artides/PMC4508301/.

Author information:Center for General Education, Chang Gung University of Science and Technology, Kweishan, Taoyuan, Taiwan, China.ln vitro and in vivo percutaneous absorption of seleno-L-methionine, an antioxidant agent, and other selenium species.Sep. 2011https://www.ncbi.nlm.nih.gov/pubmed/21785447.

Dr Vitamin SolutionsZetpil | MultiVitamin Topical Cream | VITCR1 | Cofactor—BioavailableEpub. Aug. 11, 2007.

Faculdade de Ciências Farmacêuticas de Ribeirão Preto, Universidade de São Paulo, Av. do Café, s/n, 14040-930, Ribeirão Preto, SP, Brazil.Epub Aug. 11, 2007.Enhancement of skin penetration of vitamin K using monoolein-based iquid crystalline systems.https://www.ncbi.nlm.nih.gov/pubmed/17900879.

I. Diez H. Colom J. Moreno R. Obach C. Peraire J. DomenechFirst published: Oct. 1991A comparative in vitro study of transdermal absorption of a series of calcium channel antagonistshttps://onlinelibrary.wiley.com/doi/abs/10.1002/jps.2600801006.

Karen E. Burke, Gerald F. Combs Jr., Earl G. Gross, Kailash C. Bhuyan & Hassan Abu-Libdehpublished: Aug. 4, 2009The effects of topical and oral L-selenomethionine on pigmentation and skin cancer induced by ultraviolet irradiationhttps://www.tandfonline.com/doi/abs/10.1080/01635589209514180.

Keen CL, Hurley LS.1977 AprZinc absorption through skin: correction of zinc deficiency in the rat.https://www.ncbi.nlm.nih.gov/pubmed/851081.

Kenneth J. Dillon2018Medicinal Effects of Copper Braceletshttps://www.scientiapress.com/medicinal-effects-of-copper-bracelets.

Kiran Sharma, Ashu Mittal Nitesh CauhanFeb. 1, 2015Aloe Vera as Penetration EnhancerAloe Vera as Penetration Enhancer | Insight Medical Publishinghttp://www.ijddr.inidrug-development/aloe-vera-as-penetration-enhancer.php?aid=5476.

Lee Silsby Compounding PharmacyLee Silsby Compounding Pharmacy—Experts in Compounds for BHRT, Pain and more | Crohn's—Colitishttps://www.leesilsby.com/crohns-collitis/September 10, 2012.

Lee Silsby Compunding Pharmacytransdermal B-Complex Creamhttps://www.leesilsby.com/transdermal-b-complex-cream/ September 12, 2012.

Modepalli , Shivakumar , Kanni , Murthy 2015Transdermal iron replenishment therapy.https://www.ncbi.nlm.nih.gov/pubmed/26149783.

National Academy of Sciences2011Dietary Reference Intakes (DRIs): Recommended Dietary Allowances and Adequate Intakes, Elementshttps://www.ncbi.nlm.nih.gov/books/NBK56068/table/summarytables.t3/?report=objectonly.

National Academy of Sciences2011Dietary Reference Intakes (DRIs): Recommended Dietary Allowances and Adequate Intakes, Vitaminshttps://www.ncbi.nlm.nih.gov/books/NBK56068/table/summarytables.t2/?

Philippe G. Humbert Marek Haftek Pierre Creidi Charles Lapière Betty Nusgens Alain Richard Daniel Schmitt Andre Rougier Hassan ZahouaniFirst published: Jun. 18, 2003 Topical ascorbic acid on photoaged skin. Clinical, topographical and ultrastructural evaluation: double-blind study vs. placebohttps://onlinelibrary.wiley.com/doi/abs/10.1034j.1600-0625.2003.00008.x.

'Sarah Myhill Limited2004Minerals and vitamins delivered through the skinhttp://www.drmyhill.co.uk/wiki/Minerals_and_vitamins_delivered_through_the_skin.

Seablue Vitamins2018Seablue strength dermal vitamin cream with calciumCalcium Supplements | Vitamin Absorption | Dermal Vitamin CreamLafayette, LA.

(56) References Cited

OTHER PUBLICATIONS

Giana Angelo Ph.D., Linus Pauling Institute Oregon State UniversityJan. 2013 Minerals and Skin Health https://lpi.oregonstate.edu/mic/health-disease/skin-health/minerals.

* cited by examiner

TOPICAL SUPPLEMENT COMPOSITION AND METHOD OF USE

CROSS REFERENCE TO RELATED APPLICATIONS

This application is a continuation application of U.S. patent application Ser. No. 16/229,761 filed on Dec. 21, 2018 which claims the benefit of U.S. Provisional Application No. 62/616,627 filed on Jan. 12, 2018. The above identified patent application is incorporated by reference herein in its entirety to provide continuity of disclosure.

FIELD OF THE INVENTION

The present invention relates to a topical supplement composition, and a method of applying the composition. More particularly, the present invention provides a topical supplement composition that includes zinc orotate and a transdermal carrier. The composition raises levels of vitamins, minerals and other nutrients in an individual after applying the composition to the individual's skin, whereupon components of the composition penetrate the skin and enter the bloodstream.

BACKGROUND OF THE INVENTION

A balanced diet is the best source for an individual's daily allowance of vitamins, minerals and other nutrients. However, even in populations with ready access to nutrient-rich foods, many people are unable to properly balance their diet. People ray also suffer from vitamin deficiencies caused by illness, pregnancy, digestive disorders or other conditions. Accordingly, many people take daily supplements such as multivitamins to supplement their daily intake. A multivitamin ay be advantageous over an individual vitamin, as taking an individual vitamin may result in a depletion of another vitamin. For example, consuming too much Vitamin C can break down Vitamin B12 in the digestive tract, leading to a deficiency in Vitamin B12 in the body.

Typically, supplements are taken orally in the form of a pill, tablet, or gummy. However, neurological diseases, gastric disorders or personal preference can negatively affect a person's ability to consume such an oral supplement. For example, some people have difficulty swallowing large pills and some people cannot take an oral supplement due to the texture or a perceived awful taste. As a result, the person must forgo the oral supplement or turn to alternative ethods of supplementation.

Another method of taking supplements is by direct injection. However, many individuals are averse to needles and have great difficulty in injecting medications in themselves. Some individuals may even get light-headed and faint at the sight of a needle. Additionally, supplement injections typically require the individual to measure out a dosage, which may be difficult for those with poor eyesight. These individuals may need a trained medical professional to administer their injection which can be prohibitively expensive and inconvenient.

Due to the drawbacks of supplements in the known art, there is a need in the art for an alternative supplement composition that avoids the negative aspects of oral and injection-based delivery systems. The present invention fulfills this unmet need in the art.

In view of the disadvantages inherent in the types of supplements known in the art, the present invention provides a topical supplement composition wherein the same can be utilized to deliver one or more vitamins, minerals and/or other nutrients to an individual's bloodstream by applying the composition to the individual's skin. The present topical supplement composition includes zinc orotate and a transdermal carrier. In various embodiments the one or more vitamins include one or more of Vitamin A, Vitamin B vitamins (including, but not limited to: thiamine, riboflavin, niacin, pantothenic acid, pyridoxine, biotin, adenosylcobalamin, hydroxycobalamin, and folate acid), Vitamin C, Vitamin D3, Vitamin E, and Vitamin K2.

In various embodiments, the composition includes one or more minerals, including but not limited to: Calcium, Magnesium, Iron, Copper, Selenium, and/or Zinc. In various embodiments, the composition includes one or more essential nutrients, including but not limited to: Grape Seed Oil, Rosehip Oil, Coconut Oil, and/or Hemp Seed Oil. In various embodiments, the composition includes one or more compounds, including but not limited to: Iodine, Choline, Orange Peel Essential Oil, Cetearyl Alcohol, Coco-glucoside, and/or water. In various embodiments, the transdermal carrier includes, but is not necessarily limited to, Aloe Vera Oil, Rosemary Essential Oil, and/or Eucalyptus Essential Oil. In some embodiments, Vitamin A is Retinol, Vitamin B6 is Pyridoxal-5'-phosphate, Zinc is Zinc Orotate, Calcium is Calcium Orotate, and/or Magnesium is Magnesium Orotate.

Other objects, features and advantages of the present invention will become apparent from the following detailed description.

DETAILED DESCRIPTION OF THE INVENTION

Although the characteristic features of the invention will be particularly pointed out in the claims, the invention itself and the manner in which it may be made and used may be better understood upon review of the following detailed description. Unless otherwise indicated, amounts or masses of active or inactive components of the composition are presented on a per-dosage basis (i.e., the amount per dose of the composition). Accordingly, it is contemplated that while the absolute amounts of these components may change or scale with manufacturing, packaging, or delivery of the composition of the invention, the relative amounts of these components within the composition may stay the same or nearly the same in the final product, when considered according to the per-dosage basis.

The present invention provides a topical supplement composition for delivering one or more vitamins, minerals and/or other nutrients to an individual's bloodstream by applying the composition to the individual's skin. A particular feature of the present invention is topical delivery of one or more supplement compounds from the surface of the skin to the bloodstream. This may be accomplished using any suitable transdermal carrier known, including but not limited to Aloe Vera Oil, Rosemary Essential Oil, and/or Eucalyptus Essential Oil. In this manner, the transdermal carrier may be combined with one or more vitamins, minerals, and/or other nutrients for delivery to the bloodstream, passing through the skin. This method of delivery is advantageous because the individual avoids issues encountered with oral or injection-based delivery of the supplement.

Inclusion of particular forms of vitamins or minerals may be advantageous in preparing the topical supplement composition. In some embodiments, Vitamin A may be included as Retinol, Vitamin B6 may be included as Pyridoxal-5'-phosphate, Zinc may be included as Zinc Orotate, Calcium may be included as Calcium Orotate, and/or Magnesium may be included as Magnesium Orotate.

Mineral salts of orotic acid are known as orotates. Orotates are neutrally charged and can pass through cell membranes without breaking apart. Accordingly, these orotates effectively transfer minerals across the skin barrier and the minerals associated with the salts have a high level of bioavailability. These minerals can be absorbed very efficiently into the body.

Zinc, which may be in the form of Zinc Orotate, helps form many enzymes and proteins and aids in creating new cells. Zinc also frees Vitamin A from storage in the liver. Zinc is needed for a healthy immune system and wound healing. Zinc Orotate is used to treat osteoporosis, diabetes, low white blood cell counts and lowered immunity. In one embodiment, Zinc is in the range of 2 milligrams to 40 milligrams. In one embodiment, Zinc is in the range of 2 milligrams to 20 milligrams. In another embodiment, Zinc is 15 milligrams.

Calcium, which may be in the form of Calcium Orotate, helps to build and protect bones and teeth. Calcium is also used in muscle contraction and relaxation, blood clotting and nerve impulse transmission. Typically, Calcium is obtained in the diet through milk and other dairy products, which can be problematic for individuals with a lactose intolerance. In one embodiment, Calcium is in the range of 200 milligrams to 2,500 milligrams. In one embodiment, Calcium is in the range of 200 milligrams to 1,200 milligrams. In another embodiment, Calcium is 500 milligrams.

Magnesite hich may be in the form of Magnesium Orotate, is needed for many chemical reactions in the body. Magnesium works with Calcium in muscle contraction, blood clotting and regulation of blood pressure. Magnesium helps build bones and teeth and can be helpful in cardiovascular health. In one embodiment, Magnesium is in the range of 30 milligrams to 350 milligrams. In another embodiment, Magnesium is 200 milligrams.

Iron helps hemoglobin in red blood cells, and myoglobin in muscle cells, transport oxygen throughout the body. Iron is also needed for chemical reactions and for making amino acids, neurotransmitters and hormones. In one embodiment, Iron is in the range of 0.2 milligrams to 45 milligrams. In one embodiment, Iron is in the range of 0.2 milligrams to 18 milligrams. In another embodiment, Iron is 7 milligrams.

Copper is an essential nutrient for the body. Copper aids in iron absorption and aids the immune system. Together with Iron, Copper helps make red blood cells. Copper is also incorporated into proteins. In one embodiment, Copper is in the range of 0.2 milligrams to 10 milligrams. In one embodiment, Copper is in the range of 0.2 milligrams to 2.5 milligrams. In another embodiment, Copper is 2.2 milligrams.

Selenium aids in healthy immune function, DNA synthesis, reproductive health and thyroid hormone synthesis. Selenium helps protect the body from damage caused by free radicals by acting as an antioxidant. In one embodiment, Selenium is in the range of 15 micrograms to 400 micrograms. In one embodiment, Selenium is in the range of 15 micrograms to 55 micrograms. In another embodiment, Selenium is 50 micrograms.

In addition to the plurality of minerals, the present formulation can also include a plurality of vitamins. Factors such as water solubility and fat solubility of individual vitamins limit how much an oral dose will benefit the individual's system. Water-soluble vitamins are those vitamins that are dissolved in water and are readily absorbed into the tissue, and as such are immediately available for the body to use. However, because they are immediately absorbed into the tissue, and not stored, they must be replenished regularly. If an individual were to take more water-soluble vitamin than the body needs, such excess vitamin would be secreted.

Fat-soluble molecules, such as vitamins A, D, E and K, on the other hand, can be stored in the body. Fat-soluble molecules are absorbed by lipid molecules and travel through the bloodstream. Excess fat-soluble molecules are stored in the liver and fatty tissue. Because fat-oluble molecules are stored and not excreted, taking high dosages of these molecules at once can quickly accumulate to toxic levels.

A combination of water-soluble vitamins, fat-soluble vitamins, and minerals (including orotate salts), optionally in combination with other nutrients, may not permeate the dermal layers of the skin on their own. However, when combined with a transdermal carrier, the composition crosses the dermis layer of the skin thereby enabling compounds of the composition to enter the bloodstream. Transdermal carriers, such as Aloe Vera, can be used to impart permeation of both hydrophobic as well as hydrophilic molecules. The transdermal carriers are molecules that can reversibly remove the barrier properties of the dermis and allow other molecules to penetrate the dermis and enter the circulatory system. Any and all transdermal carriers are contemplated and embodied by the present invention.

Vitamin A, which may be in the form of Retinol, is a fat-soluble vitamin. Vitamin A helps form and maintain healthy teeth, bones, soft tissues, mucous membranes and skin. Vitamin A is also important for growth, development and a healthy immune system. In one embodiment, Vitamin A is in a range of 400 micrograms to 3,000 micrograms. In another embodiment, Vitamin A is in a range of 400 micrograms to 1,300 micrograms. In another embodiment, Vitamin A is 1,200 micrograms.

Vitamin B1, which may be in the form of Thiamin, is a water-soluble vitamin. Vitamin B1 is a coenzyme that plays a central role in the release of energy from carbohydrates. Vitamin B1 aids in digestion, metabolism and normal enzyme function as well as promoting healthy skin and nerves. In one embodiment, Vitamin B1 is in a range of 0.1 milligrams to 6 milligrams. In another embodiment, Vitamin B1 is 5 milligrams.

Vitamin B2, which may be in the form of Riboflavin, is a water-soluble vitamin. Vitamin B2 is involved in the release of energy in the electron transport chain, the citric acid cycle as well as the catabolism of fatty acids. Vitamin B2 works in combination with other B-vitamins and is important for vision, skin health and converting the amino acid Tryptophan into Niacin. In one embodiment, Vitamin B2 is in a range of 0.3 milligrams to 6 milligrams. In another embodiment, Vitamin B2 is 5 milligrams.

Vitamin B3, which may be in the form of Niacin, is a water-soluble vitamin. Vitamin B3 helps release energy from carbohydrates and aids in the metabolism of lipids, proteins and carbohydrates from food. Vitamin B3 is used to treat high cholesterol and triglyceride levels and can be used to reduce the risk of heart attack. In one embodiment, Vitamin B3 is in a range of 2 milligrams to 35 milligrams. In one embodiment, Vitamin B3 is in a range of 2 milligrams to 18 milligrams. In another embodiment, Vitamin B3 is 10 milligrams.

Vitamin B6, which may be in the form of Pyridoxal-5'-phosphate is a water-soluble vitamin. Vitamin B6 serves as a co-factor in many enzyme reactions, mainly in amino acid metabolism, including the biosynthesis of neurotransmitters.

Vitamin B6 aids in the production of red blood cells, insulin and hemoglobin. In one embodiment, Vitamin B6 is in a range of 0.1 milligrams to 100 milligrams. In one embodiment, Vitamin B6 is in a range of 0.1 milligrams to 8 milligrams. In another embodiment, Vitamin B6 is 7 milligrams.

Vitamin B7, which may be in the form of Biotin, is a water-soluble vitamin. Vitamin B7 is part of an enzyme needed for synthesis of fatty acids in gluconeogenesis. Vitamin B7 helps convert food into energy by aiding in the metabolism of lipids, proteins and carbohydrates. In one embodiment, Vitamin B7 is in a range of 5 micrograms to 200 micrograms. In another embodiment, Vitamin B7 is 150 micrograms.

Vitamin B9, which may be in the form of Folinic Acid (5-Formyl tetrahydrofolate), is a water-soluble vitamin. Vitamin B9 is needed for proper brain function and aids in the production of DNA and RNA. Vitamin B9 works with Vitamins B6 and B12, and other nutrients, to control blood levels of homocysteine. In one embodiment, Vitamin B9 is in a range of 65 micrograms to 1,000 micrograms. In one embodiment, Vitamin B9 is in a range of 65 micrograms to 650 micrograms. In another embodiment, Vitamin B9 is 300 micrograms.

Vitamin B12, which may be in the form of adenosylcobalamin or hydroxycobalamin, is a water-soluble vitamin. Vitamin B12 is a co-enzyme involved in the metabolism of carbohydrates, lipids and proteins. Vitamin B12 is needed in the production of blood cells in bone marrow as well as the maintenance of the nervous system. In one embodiment, Vitamin B12 is in a range of 0.4 micrograms to 1.1 milligrams. In another embodiment, Vitamin B12 is 1 milligram.

Vitamin D is a fat-soluble vitamin. Vitamin D is very hard to get from food sources alone. Vitamin D helps the body absorb calcium and helps the body maintain proper levels of calcium and phosphorus. Vitamin D also aids in the development of teeth and bones and is itself stored in bones. In one embodiment, Vitamin D is in a range of 10 micrograms to 150 micrograms. In another embodiment, Vitamin D is 125 micrograms.

Vitamin K2, which may be in the form of Menaquinones 5% Phylloquinone), is a fat-soluble vitamin. Vitamin K2 is needed for blood coagulation and to keep bones healthy. In one embodiment, Vitamin K2 is in a range of 2 micrograms to 175 micrograms. In another embodiment, Vitamin K2 is 150 micrograms.

Vitamin C, which may be in the form of Ascorbic Acid, is a water-soluble vitamin. Vitamin C is an antioxidant that promotes healthy teeth and gums. Vitamin C helps the body absorb iron and aids in wound healing and bone formation while improving overall immune system functioning. In one embodiment, Vitamin C is in a range of 15 milligrams to 2,000 milligrams. In one embodiment, Vitamin C is in a range of 15 milligrams to 500 milligrams. In another embodiment, Vitamin C is 400 milligrams.

Vitamin E, which may be in the form of d-alpha-tocopherol, is a fat-soluble vitamin. Vitamin E is an antioxidant that helps fight infection and keeps red blood cells healthy. Vitamin E protects the skin from harmful solar radiation by acting as a free-radical scavenger. Vitamin E is typically enhanced by the inclusion of Vitamin C in a formulation. In one embodiment, Vitamin E is in a range of 4 milligrams to 1,000 milligrams. In one embodiment, Vitamin E is in a range of 4 milligrams to 150 milligrams. In another embodiment, Vitamin E is 134 milligrams.

Iodine is used as a part of thyroid hormone which helps to set the body's temperature. Iodine also influences nerve and muscle function, reproduction and growth. Some forms of Iodine, such as Povodine Iodine, are water soluble and used as a disinfectant. In one embodiment, Iodine is in the range of 10 micrograms to 1,100 micrograms. In one embodiment, Iodine is in the range of 10 micrograms to 150 micrograms. In another embodiment, Iodine is 50 micrograms.

Choline is an essential nutrient and a methyl donor. Methyl donors such as Choline decrease homocysteine levels circulating in the blood. Too many Homocysteine molecules in the blood can lead to plaque formation in the arteries. Choline is also required to make acetylcholine, a neurotransmitter.

Omega-6 fatty acids are used for reducing the risk of heart disease, lowering total cholesterol levels, lowering low-density lipoprotein ("bad cholesterol") and raising high-density lipoprotein ("good cholesterol"). In one embodiment, Grape Seed Oil and Rosehip Oil are sources of Omega-6 fatty acids. One of ordinary skill in the art will understand that other sources of Omega-6 are contemplated by this disclosure, including but not limited to vegetable oils, soybean oils, and primrose oils.

Omega-3 fatty acids are components of the phospholipids that form the structures of cell membranes. Omega-3 fatty acids also provide energy for the body and are used to form signaling molecules. In one embodiment, Hemp Seed Oil is a source of Omega-3 fatty acids. One of ordinary skill in the art will understand that other sources of Omega-3 are contemplated by this disclosure, including but not limited to Flaxseed Oil, Chia seeds, English walnuts, and Flaxseed.

Orange Peel Essential Oil can be an anti-inflammatory, an antidepressant, an antispasmodic and an antiseptic. Additionally, Orange Peel Essential Oil can be utilized for its pleasing fragrance.

Coconut Oil can be a source of medium chain triglycerides. Medium chain triglycerides are used as a quick source of energy or are turned into ketones by the body. Additionally, Coconut Oil can be utilized as an antibacterial, antifungal and moisturizer as well as for its pleasing fragrance.

The topical supplement composition can be in the form of a cream formulated to be applied to the skin of an individual. In a particular method, the individual applies the cream to an area of skin devoid of hair in order to maximize a surface area of the skin in contact with the cream. Emulsifiers can be used in concert with the vitamins, minerals and other nutrients in order to suspend and thicken the mixture. In one embodiment, Cetearyl Alcohol and Coco-glucoside can act as thickening agents of the topical supplement composition.

In one embodiment, the relative ratios between the active ingredients are:
  Vitamin A—0.078%
  Vitamin B1—0.325%
  Vitamin B2—0.325%
  Vitamin B3—0.650%
  Vitamin B6—0.455%
  Vitamin B7—0.00975%
  Vitamin B12—0.065%
  Folate—0.0195%
  Vitamin D—0.008%
  Vitamin K—0.00975%
  Vitamin C—26%
  Zinc—0.975%
  Vitamin E—8.7%
  Calcium—32.5%
  Magnesium—13%
  Iron 0.455%
  Copper—0.143%

Selenium—0.00325%
Iodine—0.00325%
Choline—16.25%

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum relationships for the components of the invention, to include variations in form, amount, concentration, and phase, are deemed readily apparent and obvious to one skilled in the art, and all equivalent relationships to those described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A topical multi-vitamin composition, comprising:
Vitamin A;
Vitamin B1;
Vitamin B2;
Vitamin B3;
Vitamin B6;
Vitamin B7;
Vitamin B9;
Vitamin B12;
Vitamin C;
Vitamin D;
Vitamin E;
Vitamin K2;
Zinc;
Calcium;
Magnesium;
Iron;
Copper;
Selenium;
Iodine;
Trimethylglycine;
Grape Seed Oil;
Rosehip Oil;
Coconut Oil;
Hemp Seed Oil;
Aloe Vera Oil;
Orange Peel Essential Oil;
Cetearyl Alcohol;
Coco-glucoside; and
Water.

2. The topical multi-vitamin composition of claim 1, wherein Vitamin A is in the form of Retinol.

3. The topical multi-vitamin composition of claim 1, wherein Vitamin B6 is in the form of Pyridoxal-5'-phosphate.

4. The topical multi-vitamin composition of claim 1, wherein Zinc is in the form of Zinc Orotate.

5. The topical multi-vitamin composition of claim 1, wherein Calcium is in the form of Calcium Orotate.

6. The topical multi-vitamin composition of claim 1, wherein Magnesium is in the form of Magnesium Orotate.

7. The topical multi-vitamin composition of claim 1, wherein:
an amount of Vitamin A is in the range of 400 micrograms to 3,000 micrograms;
an amount of Vitamin B3 is in the range of 2 milligrams to 35 milligrams;
an amount of Vitamin B6 is in the range of 0.1 milligrams to 100 milligrams;
an amount of Vitamin B9 is in the range of 65 micrograms to 1,000 micrograms;
an amount of Vitamin C is in the range of 15 milligrams to 2,000 milligrams;
an amount of Vitamin E is in the range of 4 milligrams to 1,000 milligrams;
an amount of Zinc is in the range of 2 milligrams to 40 milligrams;
an amount of Calcium is in the range of 200 milligrams to 2,500 milligrams;
an amount of Iron is in the range of 0.2 milligrams to 45 milligrams;
an amount of Copper is in the range of 0.2 milligrams to 10 milligrams;
an amount of Selenium is in the range of 15 micrograms to 400 micrograms;
an amount of Iodine is in the range of 10 micrograms to 1,100 micrograms; and
an amount of Trimethylglycine is in the range of 200 milligrams to 6,000 milligrams.

8. The topical multi-vitamin composition of claim 1, wherein:
an amount of Vitamin A is in the range of 400 micrograms to 1,300 micrograms;
an amount of Vitamin B1 is in the range of 0.1 milligrams to 6 milligrams;
an amount of Vitamin B2 is in the range of 0.3 milligrams to 6 milligrams;
an amount of Vitamin B3 is in the range of 2 milligrams to 18 milligrams;
an amount of Vitamin B6 is in the range of 0.1 milligrams to 8 milligrams;
an amount of Vitamin B7 is in the range of 5 micrograms to 200 micrograms;
an amount of Vitamin B9 is in the range of 65 micrograms to 650 micrograms;
an amount of Vitamin B12 is in the range of 0.4 micrograms to 1.1 milligrams;
an amount of Vitamin C is in the range of 15 milligrams to 500 milligrams;
an amount of Vitamin D is in the range of 10 micrograms to 150 micrograms;
an amount of Vitamin E is in the range of 4 milligrams to 150 milligrams;
an amount of Vitamin K2 is in the range of 2 micrograms to 175 micrograms;
an amount of Zinc is in the range of 2 milligrams to 20 milligrams;
an amount of Calcium is in the range of 200 milligrams to 1,200 milligrams;
an amount of Magnesium is in the range of 30 milligrams to 350 milligrams;
an amount of Iron is in the range of 0.2 milligrams to 18 milligrams;
an amount of Copper is in the range of 0.2 milligrams to 2.5 milligrams;
an amount of Selenium is in the range of 15 micrograms to 55 micrograms;
an amount of Iodine is in the range of 10 micrograms to 150 micrograms; and an amount of Trimethylglycine is in the range of 200 milligrams to 2,000 milligrams.

9. The topical multi-vitamin composition of claim 1, wherein:
an amount of Vitamin A is 1,200 micrograms;
an amount of Vitamin B1 is 5 milligrams;
an amount of Vitamin B2 is 5 milligrams;
an amount of Vitamin B3 is 10 milligrams;
an amount of Vitamin B6 is 7 milligrams;
an amount of Vitamin B7 is 150 micrograms;
an amount of Vitamin B9 is 300 micrograms;
an amount of Vitamin B12 is 1 milligram;
an amount of Vitamin C is 400 milligrams;
an amount of Vitamin D is 125 micrograms;
an amount of Vitamin E is 134 milligrams;
an amount of Vitamin K2 is 150 micrograms;
an amount of Zinc is 15 milligrams;
an amount of Calcium is 500 milligrams;
an amount of Magnesium is 200 milligrams;
an amount of Iron is 7 milligrams;
an amount of Copper is 2.2 milligrams;
an amount of Selenium is 50 micrograms;
an amount of Iodine is 50 micrograms; and
an amount of Trimethylglycine is 310 milligrams.

10. A topical multi-vitamin composition, consisting of:
Vitamin A;
Vitamin B1;
Vitamin B2;
Vitamin B3;
Vitamin B6;
Vitamin B7;
Vitamin B9;
Vitamin B12;
Vitamin C;
Vitamin D;
Vitamin E;
Vitamin K2;
Zinc;
Calcium;
Magnesium;
Iron;
Copper;
Selenium;
Iodine;
Trimethylglycine;
Grape Seed Oil;
Rosehip Oil;
Coconut Oil;
Hemp Seed Oil;
Aloe Vera Oil;
Orange Peel Essential Oil;
Cetearyl Alcohol;
Coco-glucoside; and
Water.

11. The topical multi-vitamin composition of claim 10, wherein Vitamin A is in the form of Retinal.

12. The topical multi-vitamin composition of claim 10, wherein Vitamin B6 is in the form of Pyridoxal-5'-phosphate.

13. The topical multi-vitamin composition of claim 10, wherein Zinc is in the form of Zinc Orotate.

14. The topical multi-vitamin composition of claim 10, wherein Calcium is in the form of Calcium Orotate.

15. The topical multi-vitamin composition of claim 10, wherein Magnesium is in the form of Magnesium Orotate.

16. The topical multi-vitamin composition of claim 10, wherein:
an amount of Vitamin A is in the range of 400 micrograms to 3,000 micrograms;
an amount of Vitamin B3 is in the range of 2 milligrams to 35 milligrams;
an amount of Vitamin B6 is in the range of 0.1 milligrams to 100 milligrams;
an amount of Vitamin B9 is in the range of 65 micrograms to 1,000 micrograms;
an amount of Vitamin C is in the range of 15 milligrams to 2,000 milligrams;
an amount of Vitamin E is in the range of 4 milligrams to 1,000 milligrams;
an amount of Zinc is in the range of 2 milligrams to 40 milligrams;
an amount of Calcium is in the range of 200 milligrams to 2,500 milligrams;
an amount of Iron is in the range of 0.2 milligrams to 45 milligrams;
an amount of Copper is in the range of 0.2 milligrams to 10 milligrams;
an amount of Selenium is in the range of 15 micrograms to 400 micrograms;
an amount of Iodine is in the range of 10 micrograms to 1,100 micrograms; and
an amount of Trimethylglycine is in the range of 200 milligrams to 6,000 milligrams.

17. The topical multi-vitamin composition of claim 10, wherein:
an amount of Vitamin A is in the range of 400 micrograms to 1,300 micrograms;
an amount of Vitamin B1 is in the range of 0.1 milligrams to 6 milligrams;
an amount of Vitamin B2 is in the range of 0.3 milligrams to 6 milligrams;
an amount of Vitamin B3 is in the range of 2 milligrams to 18 milligrams;
an amount of Vitamin B6 is in the range of 0.1 milligrams to 8 milligrams;
an amount of Vitamin B7 is in the range of 5 micrograms to 200 micrograms;
an amount of Vitamin B9 is in the range of 65 micrograms to 650 micrograms;
an amount of Vitamin B12 is in the range of 0.4 micrograms to 1.1 milligrams;
an amount of Vitamin C is in the range of 15 milligrams to 500 milligrams;
an amount of Vitamin D is in the range of 10 micrograms to 150 micrograms;
an amount of Vitamin F is in the range of 4 milligrams to 150 milligrams;
an amount of Vitamin K2 is in the range of 2 micrograms to 175 micrograms;
an amount of Zinc is in the range of 2 milligrams to 20 milligrams;
an amount of Calcium is in the range of 200 milligrams to 1,200 milligrams;
an amount of Magnesium is in the range of 30 milligrams to 350 milligrams;
an amount of Iron is in the range of 0.2 milligrams to 18 milligrams;
an amount of Copper is in the range of 0.2 milligrams to 2.5 milligrams;
an amount of Selenium is in the range of 15 micrograms to 55 micrograms;
an amount of Iodine is in the range of 10 micrograms to 150 micrograms; and an amount of Trimethylglycine is in the range of 200 milligrams to 2,000 milligrams.

18. The topical multi-vitamin composition of claim 10, wherein:
an amount of Vitamin A is 1,200 micrograms;
an amount of Vitamin B1 is 5 milligrams;
an amount of Vitamin B2 is 5 milligrams;
an amount of Vitamin B3 is 10 milligrams;
an amount of Vitamin B6 is 7 milligrams;
an amount of Vitamin B7 is 150 micrograms;
an amount of Vitamin B9 is 300 micrograms;
an amount of Vitamin B12 is 1 milligram;
an amount of Vitamin C is 400 milligrams;
an amount of Vitamin D is 125 micrograms;
an amount of Vitamin F is 134 milligrams;
an amount of Vitamin K2 is 150 micrograms;
an amount of Zinc is 15 milligrams;
an amount of Calcium is 500 milligrams;
an amount of Magnesium is 200 milligrams;
an amount of Iron is 7 milligrams;
an amount of Copper is 2.2 milligrams;
an amount of Selenium is 50 micrograms;
an amount of Iodine is 50 micrograms; and
an amount of Trimethylglycine is 310 milligrams.

* * * * *